United States Patent [19]

Hannam

[11] 4,356,321
[45] Oct. 26, 1982

[54] PRODUCTION OF N,N,N',N'-TETRAACETYLETHYLENEDIAMINE

[75] Inventor: Stephen J. Hannam, Clwyd, Wales

[73] Assignee: Warwick Chemical Limited, Leeds, England

[21] Appl. No.: 346,680

[22] Filed: Feb. 8, 1982

Related U.S. Application Data

[63] Continuation of Ser. No. 214,403, Dec. 8, 1980.

[30] Foreign Application Priority Data

Jun. 27, 1980 [GB] United Kingdom ............... 8021142

[51] Int. Cl.$^3$ ................ C07C 102/00; C07C 102/04
[52] U.S. Cl. .................................. 564/144; 564/153
[58] Field of Search .......................... 564/144, 133

[56] References Cited

U.S. PATENT DOCUMENTS

| 3,223,732 | 12/1965 | Viveen et al. | 564/144 |
| 3,824,286 | 7/1974 | Christiaan et al. | 564/144 X |
| 3,824,287 | 7/1974 | Matthias et al. | 564/144 |

FOREIGN PATENT DOCUMENTS

| 4919 | 10/1979 | European Pat. Off. | 564/144 |
| 907357 | 10/1962 | United Kingdom | 564/144 |
| 1335204 | 10/1973 | United Kingdom | 564/144 |
| 1378308 | 12/1974 | United Kingdom | 564/144 |
| 191560 | 3/1967 | U.S.S.R. | 564/144 |

Primary Examiner—John Doll
Attorney, Agent, or Firm—Lawrence Rosen

[57] ABSTRACT

N,N,N',N'-tetraacetylethylenediamine is made by reacting N,N'-diacetylethylenediamine with acetic anhydride and thereby forming a reaction mixture of N,N,N',N'-tetraacetylethylenediamine and acetic acid and anhydride, and distilling off acetic acid and working up the distillation residue to give substantially pure N,N,N',N'-tetraacetylethylenediamine.

9 Claims, No Drawings

PRODUCTION OF N,N,N',N'-TETRAACETYLETHYLENEDIAMINE

This application is a continuation of Ser. No. 214,403 filed Dec. 8, 1980.

This invention relates to processes for the production of TAED, which is an important auxiliary agent for use in detergents and similar compositions, where it acts as a perborate activator. In this specification TAED stands for N,N,N',N'-tetraacetylethylenediamine, DAED stands for N,N'-diacetylethylenediamine and EDA stands for ethylenediamine.

It is known to make TAED by reaction of DAED and excess acetic anhydride followed by distillation of acetic acid from the reaction mixture and separation of acetic anhydride from the TAED. It is known that this can be conducted as a cyclic process with the acetic anhydride separated in one cycle being used as a feed stock in another cycle.

The process involves an equilibrium reaction and the presence of acetic acid in the starting materials tends to suppress the yield. Unfortunately the separated acetic anhydride is contaminated with acetic acid and so yields tend to be low when using the anhydride for successive cycles. Attempts to remove all the acid results in the formation of coloured impurities and this is unacceptable. Examples are described in British Patent Specification No. 1,378,308 and European Patent Specification No. 4919.

DAED can be made by reaction of EDA with acetic acid, for instance as described in Journal Chem. Education 14, 141-2, 1939 or British Patent Specification No. 1,335,204.

It has been my object to improve the yield of TAED while obtaining a satisfactory purity level.

A process according to the invention for making TAED comprises (a) reacting DAED in a vessel with acetic anhydride and thereby forming a reaction mixture comprising TAED and acetic acid and acetic anhydride and (b) distilling the reaction mixture to remove acetic acid from the mixture, and in step (b) further acetic anhydride is added to the mixture before the distillation of the acetic acid is complete and the distillation of acetic acid is thereafter continued. By adding acetic anhydride after some acetic acid has been distilled but before the distillation of acetic acid is complete there is obtained an increase in yield disproportionate to the amount of anhydride used.

The reaction between DAED and acetic anhydride is best conducted by heating at 120° to 170° C. for 15 minutes to three hours accompanied by distillation of acetic acid from the reaction mixture. The distillation is preferably conducted until near the time when coloured by-products are formed. The amount of distillate removed is usually between 15 and 40% by volume, preferably about 25% by volume, based on the amount of acetic anhydride added to the DAED. The preferred reaction and distillation temperature is from 140° to 150° C.

When distilling acetic acid from the reaction mixture comprising TAED and acetic acid acetic anhydride is distilled off with the acetic acid and in the invention acetic anhydride is added before completion of the distillation of acid. Generally after some acetic acid has been distilled acetic anhydride is added and then further acetic acid is distilled from the mixture. Generally this is achieved by distilling acetic acid, adding an amount of acetic anhydride substantially the same as the amount of distillate that has been removed and then distilling further distillate, the amount generally being from 0.5 to 2.5, preferably 0.8 to 1.5, times the amount of distillate removed initially. The amount of distillate removed at each stage is generally between 15 and 40% by volume based on the amount of acetic anhydride added initially to the DAED.

The process may be conducted batchwise or as a cyclic or continuous process. Preferably it is conducted as a multi-cyclic process in which each cycle comprises reacting DAED in a vessel with acetic anhydride part at least of which is recovered from another cycle, thereby forming a reaction mixture of TAED and acetic acid and acetic anhydride, distilling the reaction mixture to remove acetic acid from the mixture and adding further acetic anhydride to the mixture before distillation of acetic acid is complete, and working up the distillation residue to give substantially pure TAED.

The invention is normally carried out as part of a cyclic multistep process for making TAED in which each cycle comprises reacting EDA with acetic acid to form DAED and reacting substantially all the DAED with acetic anhydride recovered from another cycle and thereby forming reaction mixture comprising TAED and acetic acid and anhydride.

The reaction between EDA and acetic acid may be conducted in the presence of acetic anhydride and is preferably conducted by mixing acetic acid and EDA, allowing the temperature to rise and distilling off the water of reaction and acetic acid, usually with additional heating.

There are described in application No. 214,404 filed even date herewith by Stephen John Hannam, John Stewart Saynor and Anthony Dennis Watling other multicyclic processes for making TAED, and the disclosure of this application is hereby incorporated by reference. Preferably the process of the present invention is conducted in conjunction with one or more of the features described in that application.

In step (a) the molar ratio of DAED:acetic anhydride in each cycle is preferably at least 1:6.

The molar ratio of DAED:acetic anhydride in each cycle is preferably always at least 1:6.5 and generally at least 1:6.8. By having such a ratio in the first cycle and maintaining it in subsequent cycles improved utilisation of reactants is obtained without formation of impurities. The ratio is generally below 1:10, preferably below 1:7.5 or 1:7.2, with best results being obtained with a ratio of about 1:7.0. Normally the described step in each cycle is carried out using the same volume of reaction mixture in which event the amount of DAED introduced into that reaction mixture for reaction in each cycle should be less than in a preceding cycle, in order to maintain the ratio DAED:acetic anhydride substantially constant.

When, as is normal, the reaction is conducted by reacting EDA with acetic acid and when, as is normal, the volume of reaction mixture in each cycle is constant the amount of EDA introduced in a subsequent cycle should be less than the amount introduced in a preceding cycle. Generally the amount introduced in second and subsequent cycles is between 30 and 90%, preferably 50 to 90% by weight of the amount introduced into the first cycle. The amount in third and any subsequent cycles may be the same as, but is generally less than (for instance being 50 to 90% by weight) of the amount used in the second cycle.

The total volume, per unit volume of reaction mixture, in step (a) of distillate distilled from the reaction mixture in one cycle is preferably more than the total volume, per unit volume of reaction mixture, in step (a) distilled from the reaction mixture in a preceding cycle. The volume of the TAED-acetic acid reaction mixture formed in each cycle is usually the same in which event the amount of distillate removed from the reaction in one cycle may be more than the amount removed in the preceding cycle. Preferably the amount is from 10 to 150% more than the amount removed in a preceding cycle. When each cycle is conducted with a single distillation stage only the amount in one cycle is generally from 10 to 60% more than the amount in the preceding cycle but when one stage is conducted with two distillation steps, as described above, and the preceding stage is conducted with a single distillation step then the total amount removed is generally from 50 to 150% more than the amount removed in the single step.

The acetic anhydride that is recovered from another cycle is generally acetic anhydride that is recovered during the working up of the distillation residue resulting from distilling acetic acid from the reaction mixture of TAED and acetic acid and anhydride. The working up may comprise phase separation, generally accompanied by cooling, of TAED from the distillation residue or other liquors containing acetic anhydride, reslurrying of TAED with acetic anhydride generally followed by phase separation, or recrystallisation of TAED from acetic anhydride and generally a combination of all three procedures is used. The liquor resulting from one or more of these procedures is recycled. Generally the working up comprises phase separation and reslurrying and these liquors are combined and recycled.

Conveniently the process is carried out in at least two and usually three or more cycles with the liquors from the working up steps in the one cycle being used for reaction with the DAED in the next cycle and with the liquors from the working up steps in the next cycle being used for reaction with the DAED in the final cycle.

The recrystallisation liquors contain for instance 7 to 10% acetic acid and impurities from the recrystallisation process and also a small amount of TAED and the trisubstituted compound. In British Specification No. 1,378,308 it is suggested that up to 5% acid based on TAED can be tolerated but we surprisingly find that 10% based on anhydride (about 70% based on DAED) can be recycled and good yield and quality obtained. Thus preferably the working up of the distillation residue comprises recrystallisation of TAED from acetic anhydride with the recrystallisation liquors being recycled for the reaction with DAED. Although the recrystallisation liquors from the final cycle can be recycled for reaction with DAED, for instance in the first cycle of another process, the other acetic anhydride containing liquors from the final cycle are generally run to waste.

The following examples illustrate the invention, Example 1 being an example of the invention and Example 2 being comparative.

EXAMPLE 1

In the first cycle 600 kg EDA and 1500 liters acetic acid are mixed and heated to distillation. Acetic acid and water is distilled off until distillation ceases at a temperature of about 150° C. and then the last traces of acetic acid are stripped by vacuum. 7000 liters of fresh acetic anhydride are charged. The temperature is raised to 140° to 150° C. and a mixture of acetic acid and acetic anhydride is distilled off until 1400 liters have been removed. 1400 liters acetic anhydride are then added and a further 1400 liters acetic acid-anhydride mixture is distilled off. The batch is cooled to 30° C. and stood to settle out the TAED. The acetic anhydride mother liquor is filtered off and the TAED is washed with acetic anhydride and then with water and is then dried. In the second cycle the process is the same except that the 7000 liters of liquid charged to the DAED is made up of mother and anhydride wash liquors from the first cycle.

The third cycle is conducted in similar manner. The yield is approximately 58% based on EDA used.

EXAMPLE 2

The process of Example 1 is repeated except that a single distillation of 1500 liters is conducted in each cycle. The yield of TAED is 3100 kg based on 1800 kg EDA, namely 45%. Thus a significant increase in yield is obtained merely by adding acetic anhydride during the distillation.

I claim:

1. A process for making TAED (N,N,N',N'-tetraacetylethylenediamine) comprising (a) reacting DAED (N,N'-diacetylethylenediamine) in a vessel with acetic anhydride, at a molar ratio of at least 1:6, and thereby forming a reaction mixture comprising TAED and acetic acid and acetic anhydride and (b) distilling the reaction mixture to remove acetic acid from the mixture, and in step (b) further acetic anhydride is added to the mixture before the distillation of the acetic acid is complete and the distillation of acetic acid is thereafter continued.

2. A process according to claim 1 carried out as a multicyclic process in which each cycle comprises (a) reacting DAED in a vessel with acetic anhydride part at least of which is recovered from another cycle and thereby forming a reaction mixture comprising TAED and acetic acid and acetic anhydride, (b) distilling the reaction mixture to remove acetic acid from the mixture, and (c) working up the distillation residue to give substantially pure TAED, and in step (b) further acetic anhydride is added to the mixture before the distillation of the acetic acid is complete and the distillation of acetic acid is thereafter continued.

3. A process according to claim 2 in which each cycle comprises the additional preliminary stage of reacting ethylenediamine with acetic acid to form DAED, and substantially all of the DAED formed is used in step (a) for reaction with acetic anhydride recovered from another cycle.

4. A process according to claim 1, claim 2 or claim 3 in which step (b) is conducted by distilling acetic acid from the mixture, then adding acetic anhydride, and then distilling further acetic acid from the mixture.

5. A process according to claim 1, claim 2 or claim 3 in which step (b) is conducted by distilling acetic acid from the mixture, then adding an amount of acetic anhydride substantially the same as the amount of distillate that has been removed from the mixture, and then distilling further acetic acid from the mixture.

6. A process according to claim 1, claim 2 or claim 3 in which step (b) is conducted by distilling from 15 to 40% by volume, based on the amount of acetic anhydride introduced for step (a), from the mixture, then adding acetic anhydride in an amount of 0.5 to 2.5 times the amount of distillate removed, and then distilling further acetic acid from the mixture.

7. A process according to claim 1, claim 2 or claim 3 in which the reaction of DAED with acetic anhydride and the distillation of acetic acid from the reaction mixture is conducted by heating the reaction mixture at 120° to 170° C.

8. A process according to claim 1, claim 2 or claim 3 in which the distillation is conducted until near the time when coloured by-products are formed.

9. A process according to claim 1 or claim 2 in which the molar ratio of DAED and acetic anhydride initially reacted is within the range of at least about 1:6 and below 1:10.

* * * * *